United States Patent [19]

Druez et al.

[11] Patent Number: 5,180,678
[45] Date of Patent: Jan. 19, 1993

[54] USES OF SUBSTANTIALLY PURE INTERLEUKIN-9 RECEPTOR

[75] Inventors: Catherine Druez, Sint-Stevens-Woluwe; Pierre Coulie, Kraainem; Catherine Uyttenhove, Chaumont-Gistoux; Jacques Van Snick, Kraainem, all of Belgium

[73] Assignee: Ludwig Institute for Cancer Research

[21] Appl. No.: 832,192

[22] Filed: Feb. 6, 1992

Related U.S. Application Data

[62] Division of Ser. No. 585,229, Sep. 19, 1990, Pat. No. 5,116,951.

[51] Int. Cl.⁵ .................... G01N 33/50; G01N 33/58; G01N 33/60; G01N 33/68
[52] U.S. Cl. ...................... 436/501; 436/63; 436/503; 436/504
[58] Field of Search ................ 530/351, 395; 514/8; 424/85.2; 436/501, 503, 63, 504

[56] References Cited

U.S. PATENT DOCUMENTS 4,578,335 3/1986 Urdal et al. ................ 530/350
4,816,565 3/1989 Honjo et al. ................ 530/351

OTHER PUBLICATIONS

Fanslow et al, "Regulation of Alloreactivity in Vivo by a Soluble Form of the IL-1 Receptor," *Science*, May 11, 1990, vol. 248, pp. 739-742.
Schmitt et al, "TCGF III/P40 is produced by naive murine CD4+ T cells ...", *Eur. J. Immunol.* 1989, vol. 19, pp. 2167-2170.
Uyttenhove et al, "Functional and structural characterization of P40 ...", *PNAS*, Sep. 1988, vol. 85, pp. 6934-6938.
Yang et al, "Expression Cloning of a cDNA Engaging a Novel Human Hematopoietic Growth Factor ...", *Blood*, Nov. 1, 1989, vol. 74(6), pp. 1880-1884.

*Primary Examiner*—Jeffrey E. Russel
*Attorney, Agent, or Firm*—Felfe & Lynch

[57] ABSTRACT

The invention relates to substantially pure interleukin 9 receptor molecules and the use thereof. The uses include use as an interleukin-9 inhibitor, as a diagnostic agent for determining interleukin-9, and as a screening agent for pharmaceuticals. The interleukin-9 receptor is characterized as a glycoprotein of about 64 kilodaltons which, upon digestion with N-glycosidase F, yields a peptide of about 54 kilodaltons.

6 Claims, 5 Drawing Sheets

94 ►

67 ►

43 ►

30 ►

20 ►

14 ►

USES OF SUBSTANTIALLY PURE INTERLEUKIN-9 RECEPTOR

This application is a divisional of Ser. Nu. 585,229 filed Sep. 19, 1990, now U.S. Pat. No. 5,116,951.

FIELD OF THE INVENTION

This invention relates to the field of lymphokines and growth factors. More particularly, it relates to a molecule referred to either as interleukin-9 ("IL-9"), or "P40", and its receptor, as well as various uses associated with this receptor.

BACKGROUND AND PRIOR ART

The last decade has seen knowledge of the immune system and its regulation expand tremendously. One area of particular interest has been that of research on the proteins and glycoproteins which regulate the immune system. Perhaps the best known of these molecules, which are generically referred to as "growth factors", "cytokines", "leukotrines", "lymphokines", etc., is interleukin-2 ("IL-2"). See, e.g., U.S. Pat. No. 4,778,879 to Mertelsmann et al.; U.S. Pat. No. 4,490,289, to Stern; U.S. Pat. No. 4,518,584, to Mark et al.; and U.S. Pat. No. 4,851,512 to Miyaji et al. Additional patents have issued which relate to interleukin 1 - ("IL-1"), such as U.S. Pat. No. 4,808,611, to Cosman. The disclosure of all of these patents are incorporated by reference herein.

In order for molecules such as IL-2 and IL-1 to exert their effect on cells, it is now pretty much accepted that these must interact with molecules, located on cell membranes, referred to as receptors. Patents which exemplify disclosures of interleukin receptors include Honjo et al., U.S. Pat. No. 4,816,565; and Urdal et al., U.S. Pat. No. 4,578,335, the disclosures of which are incorporated by reference. Recently, Fanslow, et al., Science 248: 739-41 (May 11, 1990) presented data showing that the effect of IL-1 in vivo could be regulated via the administration of a soluble form of its receptor. The last paragraph of the Fanslow paper, the disclosure of which is incorporated by reference, describes the types of therapeutic efficacy administration of a soluble IL-1 receptor ("IL-1R") is expected to have.

The lymphokine IL-9, previously referred to as "P40", is a T-cell derived molecule which was originally identified as a factor which sustained permanent antigen independent growth of T4 cell lines. See, e.g., Uyttenhove, et al., Proc. Natl. Acad. Sci. 85: 6934 (1988), and Van Snick et al., J. Exp. Med. 169: 363 (1989), the disclosures of which are incorporated by reference, as is that of Simpson et al., Eur. J. Biochem. 183: 715 (1989).

The activity of IL-9 was at first observed to act on restricted T4 cell lines, failing to show activity on CTLs or freshly isolated T cells. See, e.g., Uyttenhove et al., supra, and Schmitt et al., Eur. J. Immunol. 19: 2167 (1989). This range of activity was expanded when experiments showed that IL-9 and the molecule referred to as T cell growth Factor III ("TCGF III") are identical. IL-9 enhances the proliferative effect of bone marrow derived mast cells to "IL-3", as is described by Hültner et al., Eur. J. lmmunol. (in press), and in U.S. patent application Ser. No. 498,182 filed Mar. 23, 1990 the disclosures of both being incorporated by reference herein. It was also found that the human form of IL-9 stimulates proliferation of megakaryoblastic leukemia. See Yang et al., Blood 74: 1880 (1989).

These results point to multiple sites for reception of the IL-9 molecule rather than one on a single type of cell. As such, the invention describes a process by which the IL-9 receptor (IL-9R") was purified and characterized. The invention also describes the thus purified and characterized IL-9R molecule, as well as methods for using the molecule.

The substantially pure IL-9R of this invention is further characterized by a molecular weight of about 64 kilodaltons. It is a glycoprotein which, upon treatment with N-glycosidase F yields a peptide having a molecular weight of about 54 kilodaltons. These data are elaborated upon and explained in the disclosure which follows.

DETAILED DESCRIPTION OF PREFERRED EMBODIMENTS

Example 1

This example describes the preparation of recombinant IL-9 ("rIL-9") which was then used in experiments designed to isolate, purify, and characterize IL-9R.

Mouse IL-9 cDNA clone P40.2B4, described by Van Snick et al., supra. was subcloned into the BamHI site of baculovirus expression vector pBL941, described by Luckow et al., Virology 170: 31 (1989). Recombinant baculovirus expressing the protein of interest were isolated following Summers et al., "A manual of methods for baculovirus vectors and insect cell culture procedures", Texas Agricultural Experiment Station Bulletin No. 1555 (1988). The isolated baculovirus were used to infect Sf9 cells grown in a 4:1 mix of IPL-41 (JR Scientific) and TC 100 (Gibco) medium supplemented with 10% FBS. The resulting rIL-9 was purified in four sequential steps, and was monitored in the TS1 assay described by Uyttenhove et al., supra. The medium from infected Sf9 cells was diluted 5-fold with $H_2O$, and was adjusted to pH 5.2 via addition of 50 mM sodium acetate. This was then adsorbed onto sulfopropyl-Sephadex beads. Following washing with 20 mM NaCl and 50 mM sodium acetate (pH 5) solutions, the rIL-9 was eluted, using 0.9 M NaCl, $10^{-4}$ v/v TWEEN ® and 0.1M Tris-HCl (pH 8). Eluted material was fractionated by gel filtration on an AcA 54 column, followed by FPLC sulfopropyl cation exchange at pH 7, using 50 mM sodium phosphate. The rIL-9 represented 80% of the column bound material. Final purification was achieved using HPLC on a Vydac C4 column equilibrated in 0.05% trifluoroacetic acid, eluted with an acetonitrile gradient. This protein had a molecular weight of 22-25 kilodaltons in SDS-PAGE.

Figure 1:
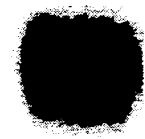
FIG. 1 shows SDS-PAGE analysis of rIL-9 produced in recombinant baculovirus containing mouse IL-9 cDNA.
Figure 2:
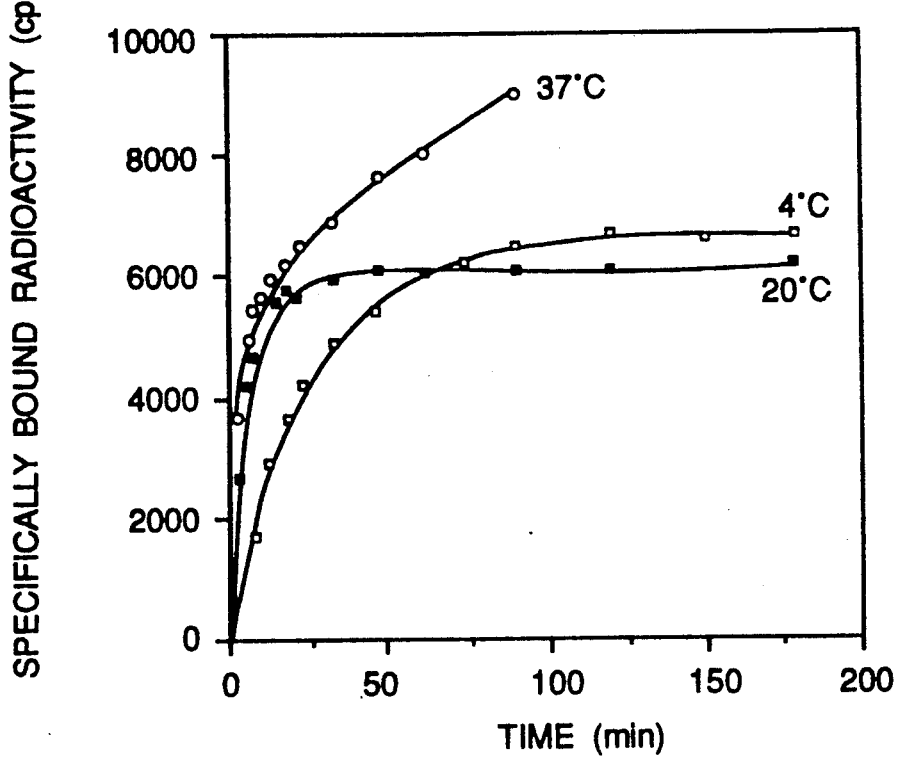
FIG. 2 shows the binding of radioactive IL-9 to TSI cells over time at various incubation temperatures.

The resulting IL-9 was labeled with $^{125}I$, using a two step procedure. Specifically, radioactive NaI (1 mCi in 50 ul of 0.1M sodium phosphate buffer, pH 7.5) was incubated for 1 minute at 4° C. in a polypropylene tube coated with iodogen. The radioactive material was then transferred to a tube containing 1-2 ug of rIL-9 in the same buffer. The reaction was quenched after 5 minutes via addition of excess, unlabelled NaI. Iodinated protein was separated from free iodide via adsorption on sulfopropyl Sephadex beads. The eluted material had a specific activity of 1-2000 cpm/fmole. Purity was verified via SDS PAGE, as shown in FIG. 1.

Example 2

In order to test whether the radioactive IL-9 would bind to TS1 cells which are mouse cells, which are IL-9 dependent, a competitive assay was carried out. Specifically, rIL-9 was incubated with TS1 cells in 140 ul of DMEM containing BSA (10 mg/ml) and $Na_3N$ (10 mM). In order to determine the level of binding, a 100 fold excess of "cold", i.e., non-radiolabelled IL-9, was also mixed with the material. The rIL-9 was admixed at $6.1 \times 10^{-10}M$, for three hours at 4° C., with $10^6$ TS1 cells. Bound material was separated from free ligand via centrifugation over a layer of dibutyl and dioctyl phthalate (15:1). In addition, the experiments were repeated using various interleukins, interferon-γ ("INF-γ"), tumor necrosis factor ("TNF"), and granulocyte, macrophage colony stimulating factor ("GM-CSF"). All experiments were carried out in triplicate. The results are set forth in Table I.

TABLE I

| Specificity of IL-9 binding to TS1 Cells | | |
|---|---|---|
| Competitor | Concentration (M) | Bound Radioactivity (cpm) |
| None |  | 4083 ± 16 |
| IL-9 | $6.1 \times 10^{-10}$ | 1181 ± 123 |
| rIL-9 | $1.2 \times 10^{-9}$ | 733 ± 21 |
| rIL-9 | $6.1 \times 10^{-8}$ | 80 ± 8 |
| IL-1α | $8.7 \times 10^{-8}$ | 4232 ± 177 |
| IL-2 | $9.3 \times 10^{-8}$ | 4255 ± 237 |
| IL-3 | $5.0 \times 10^{-8}$ | 4471 ± 7 |
| IL-4 | $8.0 \times 10^{-8}$ | 4154 ± 156 |
| IL-5 | $2.7 \times 10^{-8}$ | 4642 ± 77 |
| IL-6 | $6.7 \times 10^{-8}$ | 4751 ± 61 |
| IFN-γ | $2.4 \times 10^{-8}$ | 4944 ± 8 |
| TNF | $8.2 \times 10^{-8}$ | 4642 ± 100 |
| GM-CSF | $6.4 \times 10^{-8}$ | 4682 ± 63 |

The results show that radiolabelled rIL-9 competed with the non-radiolabelled form for binding to cells, thereby indicating the validity of continued experiments using the labelled rIL-9.

Figure 3:
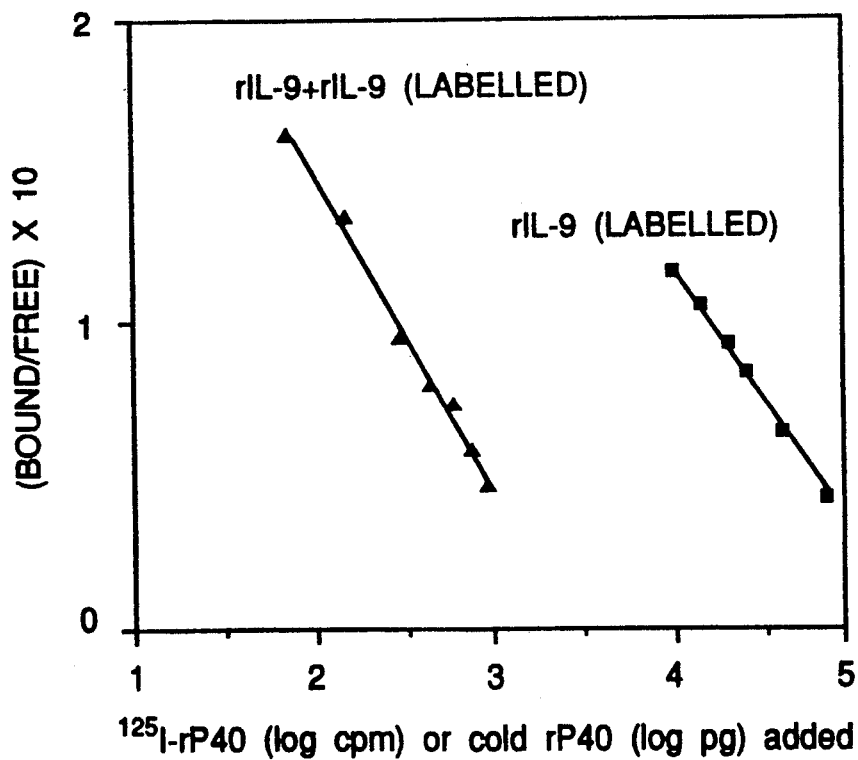
FIG. 3 shows a self displacement assay using rIL-9 and IL-9 on TS-1 cells.

FIG. 3 shows a graph of the degree of binding of labelled rIL-9, both alone and with unlabelled ligand. The data show that labeling did not alter binding characteristics.

Example 3

Figure 4A:
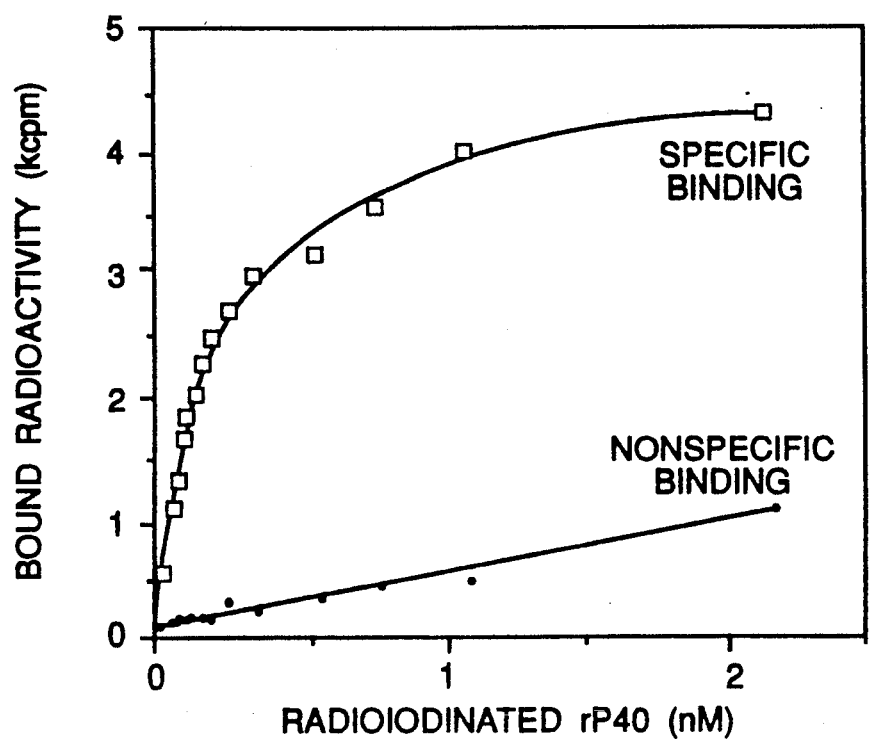
FIGS. 4a and 4b show saturation studies using TS1 cells, and Scatchard Transformation data.
Figure 4B:
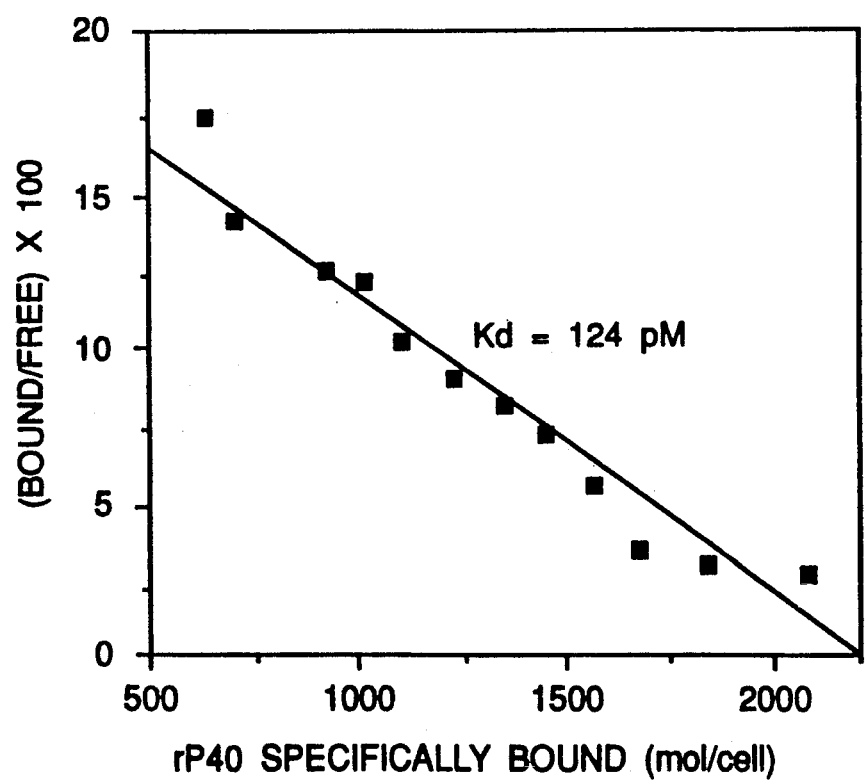

Experiments were performed to study the saturation binding of rIL-9. In these studies, as depicted in FIGS. 4a and 4b, increasing concentrations of radiolabelled rIL-9 were incubated with TS-1 cells ($5 \times 10^6$ cells, 4° C. for three hours). This binding assay, as with those described supra, used 140 ul of DMEM containing BSA and $Na_3N$, also as described supra. Binding plateaued at 1 nM concentration, with half maximal saturation being reached at approximately 100 pM (FIG. 4a). Scatchard transformation of data resulting from 3 runs of this experiment (FIG. 4b), was consistent with the existence of a single class of IL-9 receptor ("IL-9R"), one having a Kd of $103 \pm 13$ pM, and a density of $3111 \pm 565$/cell.

Example 4

It is known that when cytokines are mixed with their receptors at 37° C., they bind thereto when incubated and this is generally followed by internalization of the cytokine. This is determined via testing for increased resistance to acid induced dissociation of bound radiolabel.

To test this for the labeled rIL-9, $7 \times 10^6$ TS1 cell/ml were incubated at 4° C. in binding medium as described supra, but lacking $Na_3N$, with either $3.3 \times 10^{-10}M$ labelled rIL-9, or this concentration of the labelled cytokine plus a 100 fold excess of unlabeled rIL-9. This saturates the cells. After three hours of incubation, the cells were washed with cold binding medium to remove unbound ligand, and the cells were transferred to medium lacking rIL-9, at a temperature of 37° C. At various time intervals, the cells were incubated for two minutes with either of 360 ul of binding medium, or with citrate buffer (50 mM, pH 2.5). Contact with citrate buffer, in effect, exposed the cells to a pH of 3.0.

Figure 5:
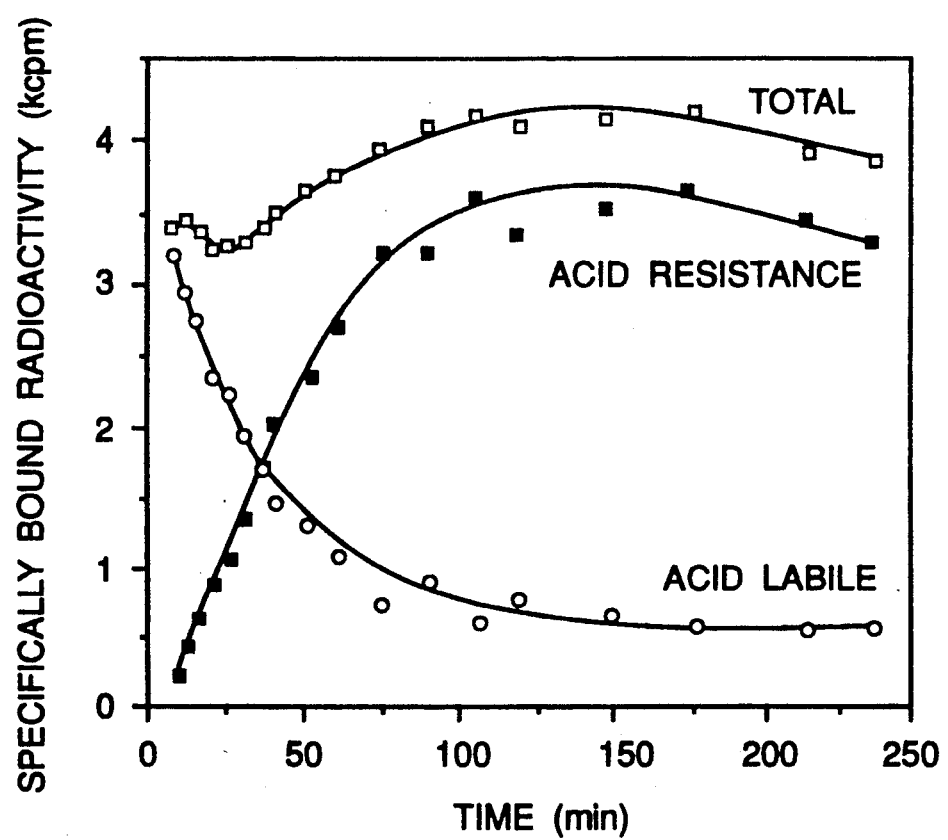
FIG. 5 denotes the degree of internalization of IL-9 over time, as demonstrated via acid lability studies.

FIG. 5 shows the results. The data prove that after about one hour, most of the IL-9 was internalized. This is consistent with the work of, e.g., Weissman et al., Proc. Natl. Acad. Sci. USA 83: 1463 (1986) (IL-2); Lowenthal et al., J. Exp. Med. 164: 1060 (IL-1); Tanaka et al., J. Immunol 140: 886 (1988) (IL-2); Lowwenthal et al., J. Immunol 140: 456 (IL-4).

Example 5

The molecular nature of the IL-9R was studied via affinity cross linking experiments. In these, $5 \times 10^6$ cells (TS1)/ml were incubated for three hours at 4° C. in 140 ul of binding medium, either with $1.3 \times 10^{-10}M$ of labeled rIL-9, or the labeled cytokine mixed with $3.1 \times 10^{-8}M$ of the unlabeled material. After two washes with 1 ml of cold, phosphate buffered saline (PBS) at pH 7.4, cells were resuspended in 2.25 ml of cold PBS (pH 8.4), containing 1 mM $MgCl_2$. Disuccinimidyl suberate, solubilized in dimethylsulfoxide, was added at a final concentration of 10 ug/ml. This cross links the cytokine to the cell. Control tests did not receive DSS. After a 30 minute incubation on ice, the reaction was quenched by adding 2.5 ml of cold 10 mM TRIS-HCl (pH 7.4) and 1 mM EDTA. The cells were centrifuged and the resulting pellet was resuspended in 50 ul of cold lysis buffer (Tris-HCl 126 mM, pH 7.5 containing 0.7% Triton-X100, 2 mM phenylmethylsulfonyl fluoride (PMSF)), 10 mM EDTA, 10 mM 2-mercaptoethanol, and, in some cases 0.2 mM pepstatin, 2 mM O-phenanthrolin and 0.1 mM leupeptin were included. This did not cause any apparent changes in the results. Following extraction, the detergent mixture was incubated for 30 minutes on ice, with insoluble material being removed by centrifuging for 15 minutes at 10,000 rpm. Supernatant was boiled for 90 seconds in the presence of 3 mg/ml of SDS, and was diluted twice with lysis buffer.

Half of this material was incubated overnight with N-glycosidase F and half was not. Following this, samples were mixed with 1 volume of 2x concentrated O'Farrell buffer, as per O'Farrell, et al., J. Biol. Chem. 250: 4007 (1974), the disclosure of which is incorporated by reference, and boiled for 5 minutes. The boiled material was then subjected to electrophoresis in 6 to 15% acrylamide gradient gels.

Figure 6:
FIG. 6 shows SDS PAGE analysis of IL-9R cross-linked to IL-9, and non cross-linked IL-9, in radiolabelled and unlabelled form.

FIG. 6 shows the results of the analysis on these gels, i.e., SDS-PAGE analysis. Referring to the lanes, lanes C and D involved tests where excess, "cold" rIL-9 was used, and all others where it was not. Lanes A and B are the product of incubation without DSS, whereas the others did use this. Lanes B, D and F represent material where the N-glycosidase F digestion was used. Thus, lanes E and F are most probative of the IL-9R molecule, because these lanes represent situations where radioactive IL-9 was used, followed by DSS cross linking. Lane F represents an experiment where the enzyme was used, so comparison of the SDS-PAGE gels for E and F gives evidence of the effect of glycosylation on the molecule.

The analysis showed two radioactive bands, of 22 and 86 kilodaltons. These correspond to the free and complexed rIL-9 molecule, respectively. When the cross linking agent was not used, or excess "cold" rIL-9 was used, the complex disappeared. This suggests that the 86 kd component contains the receptor. Treatment with N-glycosidase F reduced the weight of complex from 86 to 70 kilodaltons, and uncomplexed IL-9 from 22 to 16 kilodaltons. These results show that the receptor molecule is a glycoprotein of about 64 kilodaltons, with about 10 kilodaltons of N-linked sugars, i.e., having a protein "core" of about 54 kilodaltons.

Example 6

Following the protocols of Example 5, a number of different cell types were tested for the presence of the IL-9R molecule. Table 2, which follows, shows these results. The fact that factor dependent T-cell line TUC 7.5151, thyoma EL4.16 and mast cell line L138.8 yielded similar results, suggests that IL-9 acts on these cell types in a manner mediated by the same or similar receptors.

TABLE II

| Cellular distribution of IL-9R | | | |
|---|---|---|---|
| Cells | | IL-9R (M) | Specific Binding (mol/cell) |
| Factor-dependent T cells | TS1 | $5.6 \times 10^{-10}$ | 2235 |
| | TUC.51S1 | $1.3 \times 10^{-10}$ | 663 |
| | ST2K9.4A2 | $4.1 \times 10^{-10}$ | 1415 |
| Normal lymph nodes | | $6.2 \times 10^{-10}$ | —* |
| KLH-primed lymph nodes§ | | $6.2 \times 10^{-10}$ | — |
| Thymocytes | | $3.2 \times 10^{-10}$ | — |
| Spleen Cells | | $3.2 \times 10^{-10}$ | — |
| B lymphocytes | unstimulated** | $3.2 \times 10^{-10}$ | — |
| | LPS-blasts# | $3.2 \times 10^{-10}$ | — |
| T lymphocytes | unstimulated ‖ | $3.2 \times 10^{-10}$ | — |
| | ConA-blasts# | $3.2 \times 10^{-10}$ | — |
| CTL clones | CTL P1:5 | $1.6 \times 10^{-10}$ | — |
| | CTL P1:204 | $6.2 \times 10^{-11}$ | — |
| | CTL P35:10 | $3.3 \times 10^{-10}$ | — |
| | CTL P91:6 | $1.3 \times 10^{-10}$ | — |
| | CTL P35:48 | $1.3 \times 10^{-10}$ | — |
| Thymoma | EL4.16 | $7.5 \times 10^{-10}$ | 263 |
| | BW5147 | $6.2 \times 10^{-10}$ | 120 |
| Lymphoma | LBRM-33-1A5 | $5.6 \times 10^{-10}$ | 599 |
| T-cell leukemias | L1210 | $5.6 \times 10^{-10}$ | — |
| | LEB | $6.2 \times 10^{-11}$ | — |
| | TH1 | $5.6 \times 10^{-10}$ | 273 |
| Myelomonocytic leukemia | WEHI.3B | $7.5 \times 10^{-10}$ | — |
| B-cell hybridoma | 7TD1 | $3.2 \times 10^{-10}$ | — |
| Plasmacytoma | TEPC1033C | $3.2 \times 10^{-10}$ | — |
| Myeloid Cell Lines | DA-1 | $3.2 \times 10^{-10}$ | 18 |
| | FDC-P1 | $5.6 \times 10^{-10}$ | — |
| | Ea3,15 | $5.6 \times 10^{-10}$ | — |
| Macrophages | P399D1 | $6.2 \times 10^{-11}$ | 16 |
| | PU5-1,8 | $1.3 \times 10^{-10}$ | 229 |
| | Bone marrow derived | $4.1 \times 10^{-10}$ | 195 |
| Mast cell lines | L138.8A | $4.1 \times 10^{-10}$ | 2208 |
| | L138.C | $4.1 \times 10^{-10}$ | 331 |
| Fibroblasts | A-9 | $6.2 \times 10^{-11}$ | — |
| Fibrosarcoma | MethA | $6.2 \times 10^{-11}$ | — |
| Carcinoa | 3LL (Lewis Lung) | $6.2 \times 10^{-11}$ | — |

±Cells were incubated with $^{125}$I-labeled IL-9.
*below detection limit (<10 mol/cell)
§C57B/6 mice were immunized with 100 ug keyholed limpet hemocyanin in CFA at the base of the tail. One week later, draining lymph nodes were removed and tested for IL-9 binding.
C57BL/6 spleen cells were stimulated with ConA (4 ug/ml) or LPS (25 ug/ml). After 48h, blasts were recovered by Percoll gradient centrifugation.
‖ T cells were isolated from lymph nodes by nylon wool filtration.
**B cells were isolated from spleen cells by panning on anti-IgM-coated Petri dishes.

Example 7

The correlation between IL-9 and proliferation of T4 cell lines in response to IL-9 was studied. Resting T cells were collected from two week cultures, and $2 \times 10^6$ cells were stimulated by antigen (KLH, 25 ug/ml) in the presence of $70 \times 10^6$ & spleen cells for four days. Blasts were isolated by centrifugation and IL-9 binding was determined following incubation with $7.5 \times 10^{-10}$M labelled rIL-9. Resting cells which had not been restimulated were treated in parallel. Maximal IL-9 induced proliferation was measured by incubation of resting cells in microliter plates (50,000/well), either with or without saturating concentrations of IL-9. Radioactive thymidine incorporation, which was the manner in which proliferation was determined, was measured on day 3. Table III presents these results:

TABLE III

| Correlation IL-9 binding and proliferative responses to IL-9 in T helper clones. | | | |
|---|---|---|---|
| T helper Clones | IL-9 binding (mol/cell) | | IL-9 induced proliferation Stimulatin Index |
| | Resting Cells | Activated Cells | |
| TUC7.33 | 21 | <10 | 0.8 |
| TUC7.11 | <10 | ND | 1.1 |
| TUC2.15 | 159 | 532 | 11.2 |
| TUC7.51 | 94 | 514 | 23.8 |

Levels of IL-9 binding correlate with the ability of the cells to proliferate in response to IL-9, suggesting that expression of IL-9R is the critical event controlling IL-9 responsiveness. The data presented in Table II support this. Specifically, CTL cell lines, which have been shown not to respond to IL-9, also do not show the receptor. The presence of the receptor on some T cell tumor cell lines demonstrates that expression of the receptor is not limited to aberrant T4 helper cell lines.

The receptor was also detected on two macrophage cell lines and macrophage cultures (3 week, bone marrow), which had been cultured in the presence of macrophage colony stimulating factor suggesting that macrophages may be a target for IL-9. The presence of the IL-9R molecule on mast cell line L138.8A confirms the work of Hultner et al., supra.

The failure of non-hemopoietic cells, including fibroblast and epithelial cells to show the receptor suggests that IL-9 is a hemopoietic growth factor.

The isolated IL-9 receptor is a glycoprotein of about 64 kilodaltons which has a core peptide of about 54 kilodaltons, which binds to IL-9. The distribution of the molecule as presently known is given supra. The data show that this molecule is responsible for the reception of IL-9 by cells, as well as its internalization.

The availability of the substantially pure IL-9 receptor allows the skilled artisan to carry out a number of different methods and processes. For example, one can assay for the presence of IL-9 in samples by using the pure receptor molecule. Standard labelling techniques, such as the use of radiolabels, including $^{125}I$ as used herein, enzyme labels, metal particles, etc., as well as any of the other labels known to the art can be used. Determination of the presence of IL-9 then depends on binding to the labelled receptor molecule.

A similar approach can be taken in an assay for cells which present the IL-9 receptor. By combining IL-9, soluble receptor, and the sample, one can determine the degree to which labeled IL-9 receptor is bound, and thereby determine the amount of receptor carrying cells indirectly.

The availability of the purified receptor, in soluble form, presents therapeutic possibilities as well. The effect of IL-9 on cells is described throughout the specification. As has been shown by Fanslow, et al., Science 248: 739-741 (May 11, 1990), addition of soluble interleukin receptor (in the case of the reference, IL-1), interferes with the effect of the interleukin on the cells, since the molecule cannot bind to the cell membrane as freely. Hence, an aspect of the invention is the treatment of pathological conditions caused by proliferation of cells possessing IL-9 receptors by adding an amount of soluble IL-9 receptors sufficient to inhibit binding of IL-9 to the aforementioned cells. This methodoloqy can also be modified, and the soluble receptor can be used as a "screening agent" for pharmaceuticals. Briefly, a pharmaceutical which works by blocking the binding of IL-9 must, of course, bind to the IL-9 receptor. Prior to determining whether a material would be effective in vivo, one may use the purified IL-9R in connection with a potential pharmaceutical to determine if there is binding. If not, then the pharmaceutical may no longer be a desirable candidate. If there is in fact biding, further testing may be indicated.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. Method for determining interleukin-9 in a sample, comprising contacting said sample with labelled, substantially pure interleukin 9 receptor (IL-9R) under conditions favoring binding of interleukin 9 to said substantially pure IL9-R and determining said binding as an indication of interleukin 9 in said sample.

2. Method for determining the presence of cells which have interleukin-9 receptor (IL9-R) as a part thereof comprising contacting a cell containing sample with interleukin-9 and substantially pure IL9-R under conditions favoring binding of interleukin 9 to said cells and to said substantially pure IL9-R and determining binding of interleukin 9 to said substantially pure IL9-R as an indication of said cells in said sample.

3. Method of claim 1, wherein said labeled IL-9 receptor is labeled with a member selected from the group consisting of a radiolabel, an enzyme label, and a metal particle.

4. Method of claim 2, wherein said substantially pure Il-9 receptor is labeled with a member selected from the group consisting of a radiolabel, and enzyme label, and a metal particle.

5. Method for determining interleukin-9 receptor (IL-9R) in a sample containing cells having IL-9R on their surfaces, comprising contacting said sample with labeled isolated interleukin-9 under conditions favoring binding of interleukin-9 receptor to said labeled isolated interleukin-9 and determining said binding as an indication of interleukin-9 receptor in said sample.

6. Method of claim 5, wherein said labeled, isolated interleukin 9 is labeled with a member selected from the group consisting of a radiolabel, an enzyme label and a metal particle.

* * * * *